United States Patent
Barham et al.

(12)

(10) Patent No.: US 6,294,715 B1
(45) Date of Patent: Sep. 25, 2001

(54) HEAT TOLERANT BROCCOLI

(75) Inventors: Robert Barham, Gilroy; David Joynt, Hollister, both of CA (US)

(73) Assignee: R&D AG, Inc., Gilroy, CA (US)

( * ) Notice: Subject to any disclaimer, the term of this patent is extended or adjusted under 35 U.S.C. 154(b) by 0 days.

(21) Appl. No.: 09/328,121

(22) Filed: Jun. 8, 1999

Related U.S. Application Data

(60) Provisional application No. 60/114,038, filed on Dec. 29, 1998.

(51) Int. Cl.$^7$ ............................... A01H 5/00; A01H 5/10; A01H 4/00
(52) U.S. Cl. ......................... 800/306; 800/260; 800/298; 435/410; 435/430
(58) Field of Search ................................... 800/306, 298, 800/289, 260; 435/410, 430

(56) References Cited

U.S. PATENT DOCUMENTS 5,731,505   3/1998   Sasayama et al. ................... 800/200

OTHER PUBLICATIONS

Robertson, et al., "Regeneration of Green Comet broccoli from mesophyll protoplasts", Cruciferae Newsletter, vol. No. 9, pp. 39–40, 1984.*

Dufault, R., "Dynamic Relationships Between Field Temperatures and Broccoli Head Quality", J. Amer. Soc. Hort., Sci. 12 (4):705–710 (1996).

Sullivan, C.Y., et al., "Plant Responses to High Temperatures", Genetic Diversity in Plants, 28:301–317 (1976).

PCT Search Report, PCT/US99/31230 (Int'l Filing Date: Dec. 29, 1999).

Yang, et al., A Heat–Tolerant Broccoli $F_1$Hybrid, Ching–Long 45, HortScience 33(6):1090–1091 (1998).

Heather, D. W., et al. "Heat Tolerance and Holding Ability in Broccoli", J. Amer. Soc. Hort. Sci. 117(6); pp. 887–892 (1992).

"Broccoli," World Wide Web Page: http://www.nysaes.cornell.edu/hor . . . /bjorkman/broccoli/broccoli2.html, p. 1.

McCandless, L., Breakthrough DNA Device for Plant Breeders Developed at Cornell's Geneva Experiment Station, pp. 1–2, Cornell University, World Wide Web Page: http://www.news.cornell.edu/releases/Nov98/MatrixMill.l-m.html.

Bjorkman, Thomas et al., "High temperature arrest of inflorescence development in broccoli (*Brassica oleracea* var. italica L.)," Journal of Experimental Botany, vol. 49, No. 318, pp. 101–106, (1998) (previously cited only the abstract– disclosed herewith in its entirety).

"Broccoli," World Wide Web Page: http://aggie–horticulture.tamu.edu/plantanswers/vegetables/broccoli.html, pp. 1–3.

Wing, Lucy, "Country Living: Lucy's Country Garden: Cultivating Broccoli,", World Wide Web Page: wysiwyg://217/http://homearts.com/cl/garden/03brogfl.htm, p. 1.

Bjorkman, Thomas et al., "The heat–sensitive stage of broccoli flower development," World Wide Web Page: http//www.nysaes.cornell.edu/hort/faculty/bjorkman/broccoli/broccoli.html, pp. 1–5.

Bjorkman, Thomas et al., "High temperature arrest of inflorescence development in broccoli (*Brassica oleracea*var. italica L.)," World Wide Web Page: http://www.nysaes.cornell.edu/hort/faculty/bjorkman/other/abstracts/brocht.html, p. 1.

LeStrange, Michelle et al., "Broccoli Production in California," University of California, Division of Agriculture and Natural Resources, Publication 7211, pp. 1–3, 1996.

* cited by examiner

*Primary Examiner*—Gary Benzion
*Assistant Examiner*—Melissa L. Kimball
(74) *Attorney, Agent, or Firm*—Morrison & Foerster LLP

(57) ABSTRACT

Heat tolerant broccoli plants and seed produced therefrom are described. The heat tolerant broccoli plants are capable of producing a commercially acceptable broccoli head under heat stress growth conditions. The heat tolerant broccoli plants are exemplified by seeds deposited with the American Type Culture Collection and having ATCC Accession numbers: 203530, 203531, 203532, and 203533.

12 Claims, 1 Drawing Sheet

HEAT TOLERANT BROCCOLI

RELATED APPLICATION

This application claims the benefit under 35 U.S.C. §119 (e) of U.S. Provisional Application No. 60/114,038 filed Dec. 29, 1998.

FIELD OF THE INVENTION

This invention is in the field of plant breeding. In particular, this invention relates to the development of heat tolerant broccoli (*Brassica oleracea* L. var. *italica*).

BACKGROUND OF THE INVENTION

Broccoli (*Brassica oleracea* L. var. *italica*) has become an increasingly popular crop worldwide especially in health-conscious areas of the western world such as the North America, Europe, and Japan. An average broccoli stalk contains only 30 calories and provides 240% of the recommended daily allowance of vitamin C plus 10% of the recommended daily allowance of vitamin A. In addition to its nutritional value, some recent studies have shown that broccoli aids in the prevention of some forms of cancer.

Broccoli is a cool weather crop. High temperatures (>80° F.) for even relatively short periods of time and warm temperatures (>75° F.) for extended periods of time cause broccoli heads to be rough with uneven flower bud sizes and thus commercially unacceptable. (Björkman, T., et al. (1998) High temperature arrest of inflorescence development in broccoli (*Brassica oleracea* var. *italica* L.). Journal of Experimental Botany 49:101–106. As a result of the high sensitivity to heat during growth, broccoli can only be grown in limited areas under cool weather conditions.

Previous attempts at identifying heat tolerant broccoli cultivars have not been successful because broccoli is sensitive to relatively short periods of heat stress thereby making field observations too variable for effective genetic screening. Björkman, et al. (1998).

Thus, there is a need to develop heat tolerant broccoli varieties that will produce commercially acceptable broccoli heads under warm weather heat stress growth conditions. In addition, there is a need to develop heat tolerant broccoli inbred lines useful for producing heat tolerant F1 seed.

SUMMARY OF THE INVENTION

In order to meet these needs, the present invention is directed to heat tolerant broccoli plants. In particular, this invention is directed to broccoli seed capable of germinating and growing into a plant capable of producing a commercially acceptable head under heat stress growth conditions.

The broccoli seed of this invention are capable of germinating into a plant capable of producing a commercially acceptable head under heat stress growth conditions that render the heads of commercially available broccoli commercially unacceptable.

In addition to being heat tolerant, the broccoli seed of this invention are capable of germinating into a plant that is predominately mildew resistant.

The broccoli seed of this invention will produce a plant with a commercially acceptable head when the plant is exposed to a maximum temperature of 90° F. for at least 5 consecutive days during the growth cycle; when the plants are exposed to a maximum temperature of at least 95° F. for at least one day during the growth cycle; when the plants are exposed to a maximum temperature of 85° F. for at least 15 days during the growth cycle; when the plants are exposed to a maximum temperature of at least 75° for at least 25 days during the growth cycle; when the plants are exposed to a maximum temperature of at least 80° C. for at least 20 days during the growth cycle; and other heat stress growth conditions.

The broccoli seed of this invention include but are not limited to those seeds designated M7028, M7007, M7009, M7022, 393-2-19, H7008, H7022, 393-2-47, 98-2192, 98-2088, 98-2061, H7007, H7028, H7010, and H7021R. The broccoli seeds of this invention include inbred lines, hybrid lines, male lines and female lines, all of which are heat tolerant and capable of producing a commercially acceptable head under heat stress growth conditions.

This invention is further directed to broccoli plants or parts of broccoli plants produced from the broccoli seed of the invention. The invention is further directed to broccoli plants regenerated from tissue culture of the broccoli plants of this invention. The tissue culture of the invention comprises regenerable cells including meristematic tissue, anthers, leaves, ovules, roots, embryos, protoplasts and pollen and plants regenerated from these cells.

The invention is further directed toward transgenic heat tolerant broccoli plants. The transgenic heat tolerant broccoli lines may be resistant to various herbicides or pesticides.

The invention is further directed to broccoli plants having all of the phenotypic characteristics of the plants produced from the heat tolerant broccoli seed of the invention. The invention is further directed to plants resulting from selecting, crossing, breeding or otherwise altering the broccoli plants of this invention.

The invention is further directed to biological material isolated from the plants of this invention. Such material includes but is not limited to RNA, DNA, protein and carbohydrate. The DNA of these plants includes the gene(s) involved in heat tolerance.

This invention is further directed to the seeds and plants produced from crossing other broccoli lines with plants grown from the seed of this invention.

This invention is further directed to methods of breeding heat tolerant broccoli lines.

BRIEF DESCRIPTION OF THE DRAWINGS

The invention will be better understood by reference to the drawings in which.

DETAILED DESCRIPTION OF THE INVENTION

Figure 1:
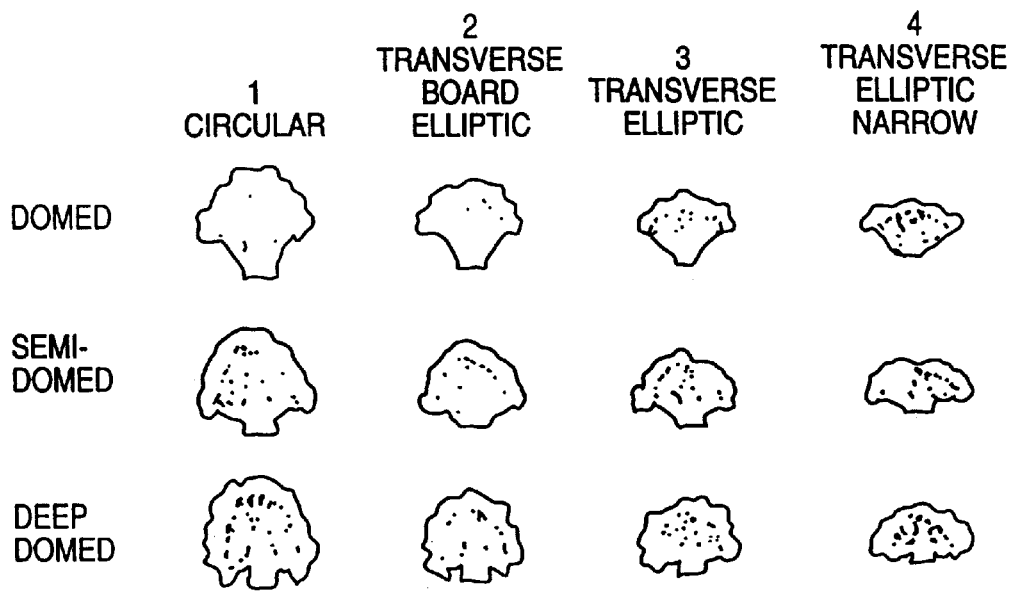
FIG. 1 shows various broccoli head shapes. Broccoli heads are referred to as domed, semi-domed and deep-domed. The shapes of the various domes are (1) circular; (2) transverse broad elliptic; (3) transverse elliptic and (4) transverse elliptic narrow.

In order to more completely understand the invention, the following definitions are provided.

Broccoli: Broccoli (*Brassica oleracea* L. var. *italica*) is a cool season vegetable in the mustard family. Principal broccoli varieties currently grown in California include, in the coastal valleys, Everest, Greenbelt, Legacy, Marathon, Ninja, Olympia, Pinnacle, Pirate, Republic, Shogun, and Sultan; in the desert valleys, Arcadia, Captain, Emperor, Everest, Galaxy, Galleon, Greenbelt, Major, Marathon, Ninja, Packman, Patriot, Pirate, and Sultan; and in the San Joaquin Valley, Arcadia, Captain, Everest, Greenbelt, Legacy, Legend, Marathon, Pirate, and Republic. Varieties grown in the Pacific Northwest are: Arcadia, Emerald City, Excelsior, Pakman Patriot, Pirate, Regal, Arcadia, Buccaneer, Emerald City, Emperor, Everest, Excelsior, Green Belt, Green Valiant, Laguna, Legend, Liberty, Major, Marathon, Pakman, Patriot, Pinnacle, Pirate, Premium Crop, Regal, Shogun, Samurai, Triathlon, Windsor. Barbados, Embassy, Green Comet, Green Defender, HMX 1134, Idol. Because of heat sensitivity, broccoli is typically grown for harvest in the spring and fall.

Commercially Acceptable Broccoli: Commercially acceptable broccoli is broccoli that distributors find acceptable for sale and consumers find acceptable for personal purchase and, ultimately, human consumption. Commercially acceptable broccoli has small uniform beads, good blue-green to green color, and tight, dome-shaped heads that extend above the leaves for ease of harvest. In commercial plantings under optimum conditions, large leafy broccoli plants produce a compact flower head on a tall, green, branching stalk. The center flower head is from 3 to 8 inches (7.5–20 cm) in diameter and plants average 24 to 36 inches (60–90 cm) tall. Hollow stems, water head rot, brown or yellow beads, bracts (leaflets) within heads, uneven bead size, and excessive branching are undesirable and commercially unacceptable defects in broccoli that can be caused by exposure to heat.

Heat Tolerant Broccoli: Heat tolerant broccoli is broccoli that will produce a commercially acceptable product when grown under heat stress growth conditions for broccoli.

Heat Stress Growth Conditions: Heat stress growth conditions for broccoli are elevated temperature growth conditions that result in broccoli that exhibit heat stress symptoms that result in a commercially unacceptable product. Heat stress symptoms include non-uniform beads; brown, yellow, light-green or purple colored heads; loose flat heads; prominent leaflets that come through the broccoli head as bracts; hollow stems; water head rot and excessive branching.

Massed: Broccoli plants are massed when a number of plants are selected and brought together for cross pollination as a group. Massing prevents further inbreeding and tends to "fix" the broccoli line at the stage from which the selections were made.

Self Pollination/Self Pollinator: Self pollination is the process of putting pollen from a plant onto a female flower or receptive female flower-part of that same plant. A plant that is a self pollinator is a plant that accepts its own pollen to make seed that typically will give rise to plants very similar or the same as the self pollinator plant. A plant that is self pollinated is said to be selfed.

Self Incompatible: A self-incompatible plant will not, under normal conditions, accept its own pollen nor generate any self seed. Self-incompatible lines are generally designated "female."

Self Compatible: A self-compatible plant accepts its own pollen and will produce self seed. Self-compatible lines are generally designated "male."

Progeny: Progeny is a broccoli line that is the offspring of the previous generation broccoli line.

Sessile: Attached to the stem by the base of the leaf.

Petiolate: Attached to the stem via a petiole.

Hybrid: The progeny of a cross fertilization between parents belonging to different genotypes.

Hybrid Vigor: The phenomenon in which the cross of two parent stocks produces hybrids that show increased vigor/heterosis compared to the parent stocks.

Inbred Lines: A nearly homozygous line produced by continuous inbreeding.

Pedigree Breeding: A system of breeding in which individual plants are selected in the segregating generations from a cross on the basis of their desirability and on the basis of a pedigree record.

The terminology used to describe the broccoli plants of this invention are generally those used by the Plant Variety Protection Office in PVP form STD-470-44 "Objective Description of Variety Broccoli (*Brassica oleracea* var. *italica*)." The following terminology is used herein.

1. Region of Adaptation (Area Where Best Adapted in USA)
(1) Northwest; (2) NorthCentral; (3) Northeast; (4) Southeast; (5) Southwest; (6) Most regions and (7) Pacific Coast.

2. Maturity (Main Crop at 50% Harvest)
Harvest Season: (1) Fall; (2) Fall/Winter; (3) Winter/Spring; (4) Spring/Summer; (5) Summer; and (6) Summer/Fall.
Spring Planted: (1) Days from Direct Seeding to 50% Harvest; (2) Days from Transplanting to 50% Harvest; and (3) Length of Harvest Period in days.
Fall Planted: (1) Days from Direct Seeding to 50% Harvest; (2) Days from Transplanting to 50% Harvest; and (3) Length of Harvest Period in days.
Time of beginning of flowering (50% of plants with at least 10% flowers: (1) Early; (2) Med-Early; (3) Medium; (4) Med-Late; and (5) Late.

3. Seedling
Cotyledon Color: (1) Yellow-Green; (2) Light Green; (3) Medium Green; (4) Dark Green; (5) Blue-Green; and (6) Purple-Green.
Cotyledon Anthocyanin: (1) Absent; (2) Weak; (3) Intermediate; and (4) Strong.
Hypocotyl Anthocyanin: (1) Absent; (2) Weak; (3) Intermediate; and (4) Strong.

4. Plant (At Harvest)
Plant Height: (cm) from soil line to top of leaves
Head Height: (cm) from soil line to top of head
Plant Branches: (1) Few; (2) Medium; and (3) Many.
Plant Habit: (1) Spreading; (2) Intermediate; and (3) Compact.
Market Class: (1) Fresh Market; (2) Processing; and (3) Both
Life Cycle: (1) Annual; (2) Biennial; and (3) Perennial.
Type of Variety: (1) Inbred; (2) Open-Pollinated; and (3) First generation Hybrid.

5. Outer Leaves (at Harvest)
Number of Leaves per Plant:
Width at midpoint of plant including petiole:
Length at midpoint of plant including petiole:
Petiole Length:
Leaf Ratio-Length/Width: (1) (2:1); (2) (3:1); (3) (4:1); (4) (5:1); and (5) (6:1).
Leaf Attachment: (1) Sessile; (2) Petiolate; and (3) Sessile and Petiolate (both).
Wax Presence: (1) None; (2) Weak; (3) Intermediate; and (4) Strong.
Foliage Color (with wax if present): 1 Light Green; (2) Medium Green; (3) Dark Green; (4) Grey-Green; (5) Blue-Green; and (6) Purple-Green.

Leaf Shape: (1) Narrow Elliptic; (2) Elliptic; and (3) Broad Elliptic.
Leaf Base: (1) Blunt and (2) Pointed.
Leaf Apex: (1) Blunt and (2) Pointed.
Leaf Margins: (1) Straight; (2) Slightly Wavy; and (3) Very Wavy.
Leaf Veins: (1) Thin; (2) Intermediate; and (3) Thick.
Midrib: (1) Not Raised; (2) Slightly Raised; and (3) Raised.
Blistering: (1) None; (2) Weak; and (3) Intermediate; and (4) Strong.
Attitude (Leaf Angle from Ground): (1) Horizontal (0–15 degrees); (3) Semi-erect (35–55 degrees); and (5) Erect (80–100 degrees).
Torsion of Leaf Tip: (1) None; (2) Weak; (3) Intermediate; and (4) Strong.
Profile of Upper Side of Leaf: (1) Concave; (2) Planar; and (3) Convex.
6. Head (At Market Maturity)
Diameter at widest point:
Depth:
Weight: market trimmed
Color: (1) Light Green; (2) Medium Green; (3) Dark Green; (4) Blue/Green; and (5) Purple.
Head Shape: (1) Circular; (2) Transverse Broad Elliptic; (3) Transverse Elliptic; and (4) Transverse Elliptic Narrow.
Dome Shape: (1) Domed; (2) Semi-domed; and (3) Deep Domed.
Head Size: (1) Small; (2) Medium; and (3) Large.
Compactness: (1) Long Pedicels (Loose); (2) Medium; and (3) Short Pedicels (Tight).
Surface Knobbling: (1) Fine; (2) Medium; and (3) Coarse.
Beads size: (1) Small; (2) Medium; and (3) Large.
Flower Buds: (1) Even in size; and (2) Uneven in size (cateye).
Anthocyanin Coloration: (1) Absent; 2 Present; (3) Leaf Axils; (4) Leaf Veins; (5) Leaf Blade; (6) Entire Plant; and (7) Leaf Petiole.
Color of Head Leaves: (1) White; (2) Green; (3) Red; and (4) Purple.
Secondary Heads: (1) Completely absent; (2) Basal; (3) Combination; and (4) Axillary along entire main stem up to main head.
Prominence of Secondary Heads: (1) Weak, (2) Intermediate; and (3)=Strong.
Number of Secondary Heads:
7. Color
Flower Color: (1) White; (2) Cream; and (3) Yellow.
Flower Stalk Color: (1) Green; (2) Purple; and (3) Variegated.
8. Disease Resistances
1=Most Susceptible
5=Intermediate
9=Most Resistant

| | |
|---|---|
| Black Leg (*Leptosphaeria maculans*) | Black Leg |
| Black Spot (Alternaria spp.) | Black Spot |
| Black Rot | Black Rot |
| Bottom Rot (*Rhizoctonia solani*) | Bottom Rot |
| Cauliflower Mosaic Virus | Cauliflower Mosaic Virus |
| Cerospora Leaf Spot (*Cercospora brassicicola*) | Cerospora Leaf Spot |
| Clubroot (*Plasmodiophora brassicae*) | Clubroot |
| Downy Mildew (*Peronospora parasitica*) | Downy Mildew |
| Erwinia Sp. | Erwinia Sp. |
| Phytophthora Root Rot (*Phytophthora megasperma*) | Phytophthora Root Rot |
| Powdery Mildew (*Erysiphe polygoni*) | Powdery Mildew |
| Pseudomonas | Pseudomonas |
| Ring Spot (*Mycosphaerella brassicicola*) | Ring Spot |
| Turnip Yellow Mosaic Virus | Turnip Yellow Mosaic Virus |
| Verticillium wilt (*Verticillium albo-atrum*) | Verticillium wilt |
| White Blister (*Albugo candida*) | White Blister |
| Xanthomonas campetis | Xanthomonas campetis |
| Yellows (*Fusarium oxysporum*) | Yellows |

9. Other Resistance
1=Most susceptible
5=Intermediate
9=Most Resistant
Insect
Buttoning
Blindness
Bolting
Brown beads
Drought
Cold
Hollow Stem
Riceyness
Whiptail
10. Heat Tolerance Heat tolerance was measured on a scale of 1–9 with 9 being the most heat tolerant and 1 being the least heat tolerant. For heat tolerance, ratings of five (5) or below are indicative of a broccoli plant that produced a commercially unacceptable head. A rating of six (6) is indicative of broccoli plants that exhibit no heat stress symptoms when exposed to 90° F. A rating of seven (7) is indicative of broccoli plants that exhibit no heat stress symptoms at 95° F. A rating of eight (8) is indicative of broccoli plants that exhibit no heat stress symptoms when exposed to 100° F. A rating of nine (9) is indicative of broccoli plants that exhibit no heat stress symptoms when exposed to 105° F.

Under some circumstances, the heat tolerant ratings are followed by a (+) or (−) to indicate a plant exhibiting symptoms slightly better (+) or slightly worse (−) than the assigned number.

Taking into account these definitions, the present invention is directed to heat tolerant broccoli plants. The heat tolerant broccoli of this invention is capable of producing a commercially acceptable product when grown under heat stress conditions.

Heat stress is exhibited in broccoli by a number of different symptoms. These symptoms include non-uniform beads; brown, yellow, light-green or purple colored heads; flat heads; bracts (leaflets in the head); rapid fracturing of the head, which reduces the harvest period; "cateye" (death of growing points), extremely small heads, and hollow stems.

Each of these symptoms is generally viewed as commercially unacceptable. The greater the number of heat stress symptoms, the more commercially unacceptable the broccoli plant. Heat stress symptoms in broccoli result from a number of interacting factors. The most important of these interacting factors are the temperature, the duration of the high temperature exposure (hours, days, weeks), the available soil moisture supply and the wind speed. Of critical importance is the timing of the exposure to the heat stress conditions during the growth cycle of broccoli. It has been shown that heat stress of broccoli can be due to an inhibition of the enlargement of broccoli bud primordia. Broccoli buds are not as sensitive to heat once they differentiate. The different heat sensitivity and resulting contrast between the delayed buds and the unaffected buds causes the uneven head appearance under heat stress growth conditions. If heat stress occurs very early in bud development (i.e., during vegetative development) no injury is generally seen. If the heat stress is applied late in bud development, many buds are affected but these buds are often obscured by the older buds.

Because of extreme sensitivity to heat stress, broccoli is generally grown in the spring and the fall when cooler temperatures are generally seen. However, a single day during the spring or fall with a high temperature of 100° F. or several warmer days (>80° F.) or multiple warm days (>75° F.) at the critical point during broccoli bud development can wipe out an entire field so that none of the heads are commercially acceptable.

The present invention is thus directed toward the development of heat tolerant broccoli varieties. The broccoli varieties of this invention will produce commercially acceptable heads grown during heat stress growth conditions during the summer months in California and other areas traditionally considered to be too warm for broccoli growth.

Broccoli Production

Broccoli may be grown by transplant production or by direct seeding. For transplant production, plants may be started in hotbeds or greenhouses. Broccoli seedlings grown in a hotbed need a loose, easily pulverized loam that is not too fertile. If the plants are started in hotbeds, soil fumigation is needed to control weeds, soil borne diseases, and insects. Seeds are planted one-quarter to one-half inch deep in rows 4 to 6 inches apart with 2 to 4 seeds per inch and covered with a sash or plastic covering. The seedlings are thinned at the two-leaf stage allowing 1½ inches between plants. Plants are watered twice daily and fertilized with soluble fertilizer at least every 2 weeks. Proper ventilation is important and can be maintained by raising the sash or plastic covering during the hottest portion of the day. In the hotbed, if properly handled, 3 or 4 ounces of seed will produce enough seedlings to plant 1 acre. When seed is planted in beds, it generally requires about 6 to 8 weeks from seed to plants for the spring crop, and about 4 to 5 weeks for the fall crop.

In the greenhouse, a variety of plant growing containers may be used (i.e. plastic cell paks, peat pots, and speedling trays) for growing broccoli. These containers can be filled with an artificial media, usually a combination of peat, perlite, vermiculite, and in some instances bark. The seeds can be sown directly into the containers and thinned upon emergence to 1 plant per cell or pot. In the greenhouse, it generally requires 5 to 6 weeks from seed to plants for the spring crop and 4 to 5 weeks for the fall crop.

For direct seeding, broccoli seeds may be direct seeded in the field using a precision planter. Seed required for one acre is generally 0.75 to 1.25 pound, when using a precision seeder.

Origin and Parentage of Heat Tolerant Broccoli Plants

The broccoli of this invention were created by classical plant breeding as well as anther culture techniques. The breeding history of the "inbred" lines identified is exemplified by the following breeding history.

| INBRED LINES | |
|---|---|
| Fall, Year 1 | Commercial broccoli hybrid Marathon was crossed with broccoli hybrid "No. 608" obtained from IM Foods, Incorporated, Gilroy, California. |
| Summer, Year 2 | F1 seed from Marathon × No. 608 were planted into row number 393 of a summer broccoli trial in Gilroy, California, and single plant selections were made for heat tolerance and downy mildew resistance. |
| Fall, Year 2 | Single plant selection number 2 from row 393, i.e. "393-2", which had exhibited good heat tolerance and downy mildew resistance, was entered into anther culture. |
| Spring, Year 3 | Anther culture product number 19 from 393-2, i.e. "393-2-19," was transplanted into the greenhouse in Gilroy, California. 393-2-19 was observed to exhibit desirable horticultural traits for deep dome-shaped head, lack of side shoots, good vigor, and high yield. 393-2-19 also demonstrated ability to produce self-pollinated seed. |
| Summer, Year 4 | The original seed from 393-2-19 made in the greenhouse in Spring, year 3, was seeded in the greenhouse in Summer, year 4, and subsequently transplanted to the field for evaluation in Gilroy, California, in the summer. 393-2-19 exhibited outstanding uniformity and was considered breeding true as a spontaneously doubled-haploid, "inbred", line. Plants were taken from the field plot for self-pollination and subsequent seed increase. |
| From Year 5 to Present | 393-2-19 has consistently exhibited exceptionally good uniformity and stability through generations of seed increase with no variants or off types plants ever observed. |

In the breeding history described above, commercial broccoli hybrid Marathon was crossed with broccoli hybrid No. 608 obtained from IM Foods, Incorporated, Gilroy, Calif. The commercially available broccoli hybrid Marathon was selected for the initial cross because it had demonstrated good yield potential. Hybrid No. 608 was selected for the initial cross because it was thought to have less side shoots, an advantageous characteristic for harvesting.

During the breeding process, F1 seed from Marathon×No. 608 were planted and grown. Selections were made for heat tolerance and downy mildew resistance. The heat tolerance selection was conducted at head formation through harvest maturity. The selection criteria were smooth domed head, even flower-bud size, good head color, lack of bracting (leaflets in the head), and an ability to hold a good head shape through harvest maturity. The downy mildew selection was conducted throughout the growth cycle of the plants. The selection for downy mildew resistance was based on plants with no mildew lesions or a greatly reduced number of lesions present on any leaves as compared to non-resistant plants.

Multiple single plant selections exhibiting heat tolerance and downy mildew resistance were entered into anther culture. In this procedure, the undifferentiated pollen mother cells that exist in immature broccoli anthers are stimulated in vitro into embryonic states by procedures well known in the literature. The undifferentiated pollen mother cells are subjected to treatments of higher temperatures, light and dark and specialized media growth conditions including hormone simulation. Plant growth conditions of 60° F. and bright light followed by a heat shock of 90° F. after anther excision and culturing can help stimulate embryogenisis. This process can stimulate the development of embryonic growth wherein the haploid (one-half the chromosome number) pollen mother cell multiplies and grows into callus tissue. The callus tissue, through the use of specialized media, hormone treatments, ard controlled temperature and light can be stimulated to make green plant shoots and eventually functional roots. Some of these haploids spontaneously double their chromosome number, thus; generating "di-haploids," which are essentially completely homozygous. These highly homozygous lines are genetically equivalent to the end result of many years of self-pollination by conventional means.

The anther culture material was grown and then transplanted into the greenhouse for further selections. Various plants were selected based on desired phenotypical characteristics including an ability to produce self-pollinated seed. Self-pollination is advantageous because it permits seed increase and bulking of seed without random cross-pollination.

Male Lines

Numerous heat tolerant "male" broccoli lines have been identified and shown to be stable and uniform. For illustrative but non-limiting purposes, the breeding histories of the M7007, M7009 and M7028 are provided as follows.

The "Cruiser" broccoli line was selected for initial crosses because it was a commercially available hybrid that showed a small degree of heat tolerance which was rated at approximately 5 and also had a nicely elevated head.

M7007

| | |
|---|---|
| Year One | IM Hybrid No. 608 obtained from IM Foods, Incorporated, Gilroy, California, was self-pollinated. |
| Year Two | F2 of Hybrid No. 608 is crossed with Cruiser which was obtained from Royal Sluis, a Dutch seed company. |
| Year Three | Heat tolerant single plant selection of the F2 Hybrid 608/Cruiser with heat tolerance equaling 8- was made. |
| Year Four | Heat tolerance equaling 7 + single plant selection gives [(No. 608) F2/Cruiser] F3. |
| Year Five | Eight selections are selfed and massed selected to give [(No. 608) F2/Cruiser] F4. |
| Year Six | Twelve selections are massed. |
| Year Seven | Fifteen selections are massed. |
| Year Eight | Five selections are massed selected and entered into a large isolation cage increase to give the finished line M7007. |

M7009

| | |
|---|---|
| Year One | IM Hybrid No. 608 is self-pollinated. |
| Year Two | F2 of Hybrid No. 608 is crossed with Cruiser. |
| Year Three | Heat tolerant single plant selection of the F2 Hybrid 608/Cruiser with heat tolerance equaling 8- was made. |
| Year Four | Heat tolerance equaling 7 + single plant selection gives [(No. 608) F2/Cruiser] F3. |
| Year Five | Eight selections are selfed and massed to give [(No. 608) F2/Cruiser] F4. |
| Year Six | Twelve selections are massed. |
| Year Seven | Fifteen selections are massed. |
| Year Eight | Five selections are massed selected and entered into a large isolation cage increase to give the finished line. |
| Year Nine | Seed storage. |
| Year Ten | Six selections are massed selected and entered into a large isolation cage increase to give finish line M7009. |

M7028

| | |
|---|---|
| Year Two | F2 of Hybrid No. 608 is crossed with Cruiser. |
| Year Three | Heat tolerant single plant selection of the F2 Hybrid 608/Cruiser with heat tolerance equaling 8- was made. |
| Year Four | Made single plant selection. [(No. 608) F2/Cruiser] F3 |
| Year Five | Made single plant selection with heat tolerance equaling 7. [(No. 608) F2/Cruiser] F4 |
| Year Six | Made single plant selection with heat tolerance equaling 7. [(No. 608) F2/Cruiser] F5 |
| Year Seven | Selected five plants, massed selected and entered into a large isolation cage to give finished line M7028. |

The male lines of this invention can be crossed with female lines to produce hybrid seed. The female lines may or may not be heat tolerant. Encompassed within the scope of this invention are the hybrid seed produced from crossing the male lines of this invention with other broccoli lines of interest. Hybrid seed includes but is not limited to H7007, H7008, H7028.

Hybrid Seed Production

For hybrid seed production of heat tolerant broccoli seed, two lines are selected for production. The lines are designated male or female, with the female being the recipient of the male line pollen. Either the male or female or both lines may be heat tolerant as defined by this invention. Broccoli plants flower with both the female and male parts and are capable of self-pollination. The line designated "female" is generally "self-incompatible," which means it will not accept its own pollen, a process developed in the plant by breeding. The line designated "male" is generally "self-compatible" and will accept its own pollen. Since self-incompatible lines will not accept their own pollen, but will out-cross with other broccoli pollen, they produce the commercially desired hybrid seed. The male line is the pollen provider to the female line. The cross of the self-compatible male line and the self-incompatible female line will produce a seed, which is a hybrid.

Once a hybrid has been selected for seed production, a "nick" study is done. The nick study identifies the flowering period of the female, i.e. when it will start to flower and for how long it will flower. The same is done for the male line and the two are compared. In all cases, the female will flower longer then the male. The nick study gives the data needed to determine if the female will require 2, 3, or 4 male planting dates to cover its full flowering period.

Once the data from the nick study is obtained, seed of the female and the first male are planted in the greenhouse. The second male is planted in the greenhouse 7–10 days later, with the third male planted another 7–10 days after that, and the final or $4^{th}$ male planted within 10 more days. The female is seeded in the greenhouse at 11,000 plants for each production acre and each male planting at 7,000 plants. Forty-five days from being planted in the greenhouse the female and first male are ready for transplanting in the field. The three remaining males are each transplanted into the field within 45 days of their individual greenhouse planting dates.

Field Production of Hybrid Seed

Figure 2:
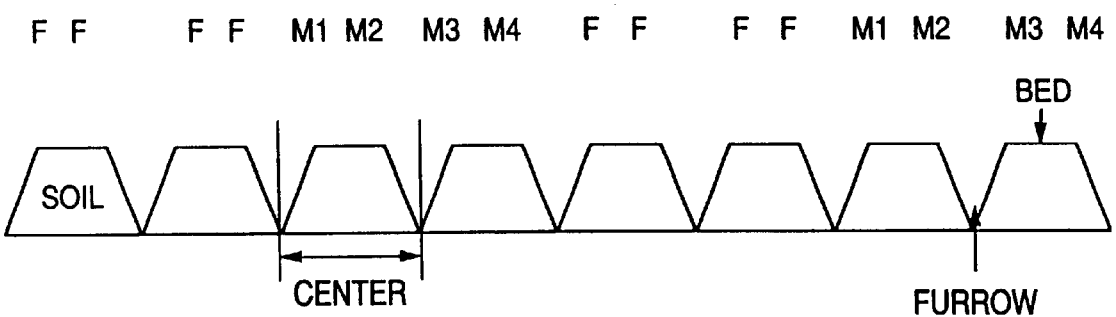
FIG. 2 shows a cross section of eight 40-inch beds utilized for field production of the hybrid seed of this invention. In this diagram: F=female line seed-line; M1=first male planting seed-line; M2=second male planting seed-line; M3=third male planting seed-line and M4=fourth male planting seed-line.

Field production of the hybrid seed is begun when all of the female plants and the first male plants from the greenhouse are transplanted into the field. Transplanting can be done by machine or by hand with large crews. The plants are placed into the soil on prepared listed beds that are on 40-inch centers (see FIG. 2). The depth of the planting is generally 3 inches, but depends on the size of the transplant plug. Each plant is separated approximately eighteen inches apart going down the seed-line and each parallel seed-line on a single bed is twelve inches apart. The successive plantings of the second, third, and fourth male follow the female planting at approximately ten day intervals. An illustrative planting schedule is as follows:

| | |
|---|---|
| October 15 | female transplanting date |
| October 15 | first male transplanting date |
| October 25 | second male transplanting date |
| November 4 | third male transplanting date |
| November 14 | fourth male transplanting date |

The dates are not fixed, but are an approximation for illustrative and non-limiting purposes.

Once all the plantings are accomplished, the field is watched for typical cultural problems found in all broccoli production, whether for seed or vegetable. These problems include weeds, diseases, insect pests, irrigation, fertilization, and cultivation.

The singular difference for a seed production field as compared to a broccoli production field is the use of rogueing. Rogueing is simply the walking and examination of a field and checking each plant for correctness to type. Any plant that does not fit the proper description for type is pulled and destroyed or "rogued." The roguing starts within thirty days of the last male transplanted and continues until the field is at a market ready point, which is generally 100 days. Once the field is at market ready (market ready being the point where the heads are harvestable as a vegetable for sale) the seed production starts. Market ready heads are generally seen in the female and first male in late April to early May of the year following transplanting. The fully developed heads will begin to age and then bolt, which is the extension of individual flower stalks. The nick or timing between the male plants bolting and female plants bolting is now the crucial item watched. The female will only set hybrid seed if pollen is in constant and abundant supply from a male plant. The heads of both the male and female plant can be trimmed to accelerate or slow down the flowering to insure abundant male flowers are available as the female plant flowers. Pollen transfer from the male to the female is done by honeybees, which are commercially supplied. Each acre of seed production requires three to five hives of honeybees. The flowering stage will last sixty to eighty days.

The flowering period is followed by the maturation of the seed within seedpods. The maturation period of 40 to 60 days is checked by monitoring the seed development, as it goes from green and water filled, to the dough stage ending with the seed turning from green to brown in color. A judgment call is taken, measuring the number of the mature seeds versus seeds yet completed. When the majority of the seed is mature the female plants are cut by hand and laid in rows (windrowed) to dry down for combining. Ten to twenty days are needed for the plants to dry down.

Combining is a process which entails the use of a large harvest machine that lifts the broccoli plants from the ground and grinds them for seed preparation. The plant material is cleaned away from the seed by screens and air, leaving only seed. Combining is the initiation of the seed re-conditioning process. Once combined or harvested, the seed is sent to a mill, which further cleans the seed, separates the clean seed by size and weight within a size. All testing for purity, disease, germination, and percent hybridity is done on the clean, sized, and weighted seed. If the seed passes the testing it is canned and sold.

The above method describes the seed production methods for the specific hybrids H7007, H7009 and H7028 and generally is the method used for all other hybrid broccoli seed production. Hybrid seeds H7007, H7009 and H7009 were produced by crossing corresponding male lines with 393-2-19 as follows:

H7007=393-2-19×male 7007
H7009=393-2-19×male 7009
H7028=393-2-19×male 7028

Comparative Studies

Several studies have been performed to compare and contrast the broccoli lines of this invention with the commercially available broccoli line.

Comparative Analysis Study #1

In study #1, the following broccoli lines were analyzed: Hybrid 7007, hybrid 7008, hybrid 7022, hybrid 7028, male 7007, male 7009, male 7022, male 7028, hybrid 393-2-19, hybrid 393-2-47, Marathon and Pinnacle. Marathon and Pinnacle are commercially available broccoli hybrids.

Broccoli seeds were sown in the greenhouse. Broccoli seedlings were transplanted to the field on August 8. Daily high and low temperature measurements during the course of study #1 are presented in Table 1. Note that the growing temperatures for study #1 were generally quite warm.

In study #1, the days from direct seeding to 50% harvest; days from transplanting to 50% harvest and the length of the harvest period are shown in Table 2.1. The results indicate that the broccoli lines of this invention have a significantly longer harvest period than the commercially available hybrids Marathon and Pinnacle. A longer harvest period offers growers greater flexibility in harvesting and therefore greatly reduces costs.

Table 2.2 shows data summarizing various characteristics of the broccoli plants at harvest. Tables 2.3A and 2.3B show data regarding the characteristics of the outer leaves at harvest. The data indicate that both Pinnacle and Marathon were gray-green in foliage color, which is demonstratively different and less commercially acceptable than the blue green foliage of the heat tolerant lines of the invention.

Table 2.4A–2.4D show characteristics of the broccoli heads at market maturity. Table 2.5 shows flower color.

Table 2.6 shows resistance to various environmental conditions, undesirable characteristics of broccoli and diseases. Of particular importance is that the commercially available varieties Marathon and Pinnacle are much more susceptible to downy mildew virus as compared to the broccoli lines of the invention.

Table 2.7 shows heat tolerance data. Of particular relevance is the low heat tolerance of the commercially available varieties Marathon and Pinnacle as compared to the broccoli lines of this invention.

TABLE 1

Temperature Data for Study #1

| Date | Temperature (° F.) | | |
|---|---|---|---|
| | Max | min | Average |
| 07/03 | 79 | 47 | 62 |
| 07/04 | 84 | 48 | 63 |
| 07/05 | 75 | 52 | 60 |
| 07/06 | 75 | 52 | 62 |
| 07/07 | 75 | 52 | 61 |
| 07/08 | 71 | 48 | 59 |
| 07/09 | 63 | 54 | 58 |
| 07/10 | 70 | 54 | 59 |
| 07/11 | 73 | 53 | 59 |
| 07/12 | 74 | 52 | 59 |
| 07/13 | 85 | 53 | 65 |
| 07/14 | 87 | 54 | 69 |
| 07/15 | 82 | 50 | 63 |
| 07/16 | 72 | 32 | 62 |
| 07/17 | 76 | 56 | 64 |
| 07/18 | 83 | 58 | 68 |
| 07/19 | 89 | 52 | 69 |
| 07/20 | 83 | 53 | 67 |
| 07/21 | 88 | 53 | 71 |
| 07/22 | 100 | 55 | 78 |
| 07/23 | 99 | 59 | 77 |
| 07/24 | 88 | 56 | 69 |
| 07/25 | 95 | 54 | 72 |
| 07/26 | 81 | 58 | 70 |
| 07/27 | 76 | 55 | 63 |
| 07/28 | 78 | 55 | 62 |
| 07/29 | 75 | 56 | 62 |
| 07/30 | 72 | 56 | 61 |
| 07/31 | 72 | 57 | 62 |

TABLE 1-continued

Temperature Data for Study #1

| | Temperature (° F.) | | |
|---|---|---|---|
| Date | Max | min | Average |
| 08/01 | 82 | 57 | 65 |
| 08/02 | 83 | 56 | 65 |
| 08/03 | 88 | 54 | 68 |
| 08/04 | 83 | 56 | 66 |
| 08/05 | 77 | 56 | 64 |
| 08/06 | 74 | 58 | 64 |
| 08/07 | 79 | 59 | 66 |
| 08/08 | 90 | 56 | 71 |
| 08/09 | 98 | 59 | 74 |
| 08/10 | 109 | 60 | 81 |
| 08/11 | 100 | 61 | 78 |
| 08/12 | 91 | 58 | 70 |
| 08/13 | 83 | 56 | 66 |
| 08/14 | 84 | 52 | 64 |
| 08/15 | 81 | 50 | 62 |
| 08/16 | 86 | 50 | 66 |
| 08/17 | 92 | 53 | 71 |
| 08/18 | 98 | 58 | 75 |
| 08/19 | 97 | 60 | 75 |
| 08/20 | 92 | 57 | 71 |
| 08/21 | 89 | 58 | 68 |
| 08/22 | 74 | 54 | 61 |
| 08/23 | 74 | 53 | 61 |
| 08/24 | 72 | 51 | 61 |
| 08/25 | 69 | 53 | 60 |
| 08/26 | 71 | 52 | 60 |
| 08/27 | 77 | 54 | 63 |
| 08/28 | 81 | 50 | 63 |
| 08/29 | 86 | 51 | 67 |

TABLE 1-continued

Temperature Data for Study #1

| | Temperature (° F.) | | |
|---|---|---|---|
| Date | Max | min | Average |
| 08/30 | 87 | 50 | 67 |
| 08/31 | 83 | 51 | 64 |
| 09/01 | 69 | 54 | 59 |
| 09/02 | 81 | 51 | 61 |
| 09/03 | 91 | 48 | 64 |
| 09/04 | 95 | 52 | 71 |
| 09/05 | 94 | 46 | 72 |
| 09/06 | 95 | 57 | 71 |
| 09/07 | 91 | 55 | 69 |
| 09/08 | 93 | 54 | 71 |
| 09/09 | 98 | 54 | 69 |
| 09/10 | 91 | 58 | 71 |
| 09/11 | 83 | 61 | 69 |
| 09/12 | 89 | 64 | 73 |
| 09/13 | 95 | 68 | 77 |
| 09/14 | 93 | 64 | 75 |
| 09/15 | 77 | 56 | 64 |
| 09/16 | 68 | 56 | 60 |
| 09/17 | 83 | 32 | 70 |
| 09/18 | 85 | 52 | 67 |
| 09/19 | 87 | 55 | 69 |
| 09/20 | 88 | 57 | 68 |
| 09/21 | 76 | 55 | 62 |
| 09/22 | 73 | 53 | 61 |

TABLE 2

Comparative Analysis (Study #1)

2.1. Region of Adaption/Maturity Main Crop at 50% Harvest

| # | I.D. | Region of Adaption | Days from Direct Seeding to 50% Harvest | Days from Transplanting to 50% Harvest | Length of Harvest Period in Days |
|---|---|---|---|---|---|
| 1 | Hybrid 7007 | Most regions | 137 | 84 | 7 |
| 2 | Hybrid 7008 | Most regions | 137 | 87 | 6 |
| 3 | Hybrid 7022 | Most regions | 127 | 77 | 6 |
| 4 | Hybrid 7028 | Most regions | 136 | 86 | 6 |
| 5 | Male 7007 | Southwest | 135 | 85 | 3 |
| 6 | Male 7009 | Southwest | 135 | 85 | 4 |
| 7 | Male 7022 | Southwest | 123 | 73 | 5 |
| 8 | Male 7028 | Southwest | 138 | 88 | 5 |
| 9 | Inbred 393-2-19 | Most regions | 137 | 87 | 8 |
| 10 | Inbred 393-2-47 | Most regions | 133 | 83 | 6 |
| 11 | Marathon | Most regions | 134 | 84 | 4 |
| 12 | Pinnacle | Southwest | 123 | 73 | 2 |

2.2. Study #1
Plant (At Harvest)

| # | I.D. | Plant Height (cm) | Head Height (cm) | Plant Branches | Plant Habit | Market Class | Lifecycle | Variety Type |
|---|---|---|---|---|---|---|---|---|
| 1 | Hybrid 7007 | 76.5 | 57.5 | Few | Intermediate | Fresh Market/Processing | Annual | First generation hybrid |
| 2 | Hybrid 7008 | — | — | — | — | — | — | — |
| 3 | Hybrid 7022 | 72 | 51.5 | Few | Spreading | Fresh Market/Processing | Annual | First generation hybrid |
| 4 | Hybrid 7028 | 82.5 | 57.5 | Few | Intermediate | Fresh Market/Processing | Annual | First generation hybrid |
| 5 | Male 7007 | 92 | 65 | Few | Intermediate | Fresh Market/Processing | Annual | Inbred |
| 6 | Male 7009 | 92 | 76 | Few | Intermediate | Fresh Market/Processing | Annual | Inbred |
| 7 | Male 7022 | 58 | 35 | Few | Compact | Fresh Market/Processing | Annual | Inbred |
| 8 | Male 7028 | 74.5 | 51 | Few | Intermediate | Fresh Market/Processing | Annual | Inbred |
| 9 | Inbred 393-2-19 | 62 | 45.5 | Few | Intermediate | Fresh Market/Processing | Annual | Inbred |
| 10 | Inbred 393-2-47 | 60 | 48.5 | Few | Intermediate | Fresh Market/Processing | Annual | Inbred |
| 11 | Marathon | 86.5 | 56.5 | Medium | Spreading | Fresh Market/Processing | Annual | First generation hybrid |
| 12 | Pinnacle | 88.5 | 61.5 | Few | Intermediate | Fresh Market/Processing | Annual | First generation hybrid |

2.3A. Study #1
Outer Leaves (At Harvest)

| # | I.D. | # Leaves Per Plant | Leaf Width (cm) | Leaf Length (cm) | Petiole Length (cm) | Leaf Attachment | Wax Presence | Foliage Color |
|---|---|---|---|---|---|---|---|---|
| 1 | Hybrid 7007 | 29 | 20 | 52.5 | 22 | Petiolate | Strong | Blue-green |
| 2 | Hybrid 7008 | — | — | — | — | — | — | — |
| 3 | Hybrid 7022 | 18 | 14 | 41 | 17.5 | Petiolate | Strong | Blue-green |
| 4 | Hybrid 7028 | 25 | 17.5 | 53.5 | 19.5 | Petiolate | Strong | Blue-green |
| b | Male 7007 | 30 | 16.5 | 40.5 | 13.5 | Petiolate | Strong | Blue-green |
| 6 | Male 7009 | 26 | 15.5 | 47 | 18 | Petiolate | Strong | Blue-green |
| 7 | Male 7022 | 21 | 23.5 | 48 | 17.5 | Petiolate | Strong | Blue-green |
| 8 | Male 7028 | 34 | 15.5 | 42.5 | 19. | Petiolate | Strong | Blue-green |
| 9 | Inbred 393-2-19 | 23 | 14 | 36 | 11.5 | Petiolate | Strong | Blue-green |
| 10 | Inbred 393-2-47 | 24 | 16.5 | 40 | 17.5 | Petiolate | Strong | Blue-green |
| 11 | Marathon | 50 | 15.5 | 50 | 22 | Petiolate | Intermediate | Grey-green |
| 12 | Pinnacle | 27 | 16 | 46.5 | 21 | Petiolate | Intermediate | Grey-green |

2.3B. Study #1
Outer Leaves (At Harvest)

| # | I.D. | Leaf Shape | Leaf Base | Leaf Apex | Leaf Margins | Leaf Veins | Midrib | Blistering | Attitude | Leaf tip Torsion | Upper Side of Leaf Profile |
|---|---|---|---|---|---|---|---|---|---|---|---|
| 1 | Hybrid 7007 | Elliptic | Blunt | Blunt | Slightly wavy | Intermediate | Slightly raised | None | Semi-erect | Weak | Concave |
| 2 | Hybrid 7008 | — | — | — | — | — | — | — | — | — | — |
| 3 | Hybrid 7022 | Narrow elliptic | Blunt | Blunt | Slightly wavy | Intermediate | Slightly raised | None | Semi-erect | None | Planar |

-continued

2.3B. Study #1
Outer Leaves (At Harvest)

| # | I.D. | Leaf Shape | Leaf Base | Leaf Apex | Leaf Margins | Leaf Veins | Midrib | Blistering | Attitude | Leaf tip Torsion | Upper Side of Leaf Profile |
|---|------|-----------|-----------|-----------|--------------|------------|--------|------------|----------|------------------|----------------------------|
| 4 | Hybrid 7028 | Elliptic | Blunt | Blunt | Slightly wavy | Intermediate | Slightly raised | None | Semi-erect | None | Concave |
| 5 | Male 7007 | Elliptic | Blunt | Blunt | Slightly wavy | Intermediate | Slightly raised | None | Erect | Weak | Concave |
| 6 | Male 7009 | Elliptic | Pointed | Blunt | Slightly wavy | Intermediate | Slightly raised | None | Erect | Intermediate | Planar |
| 7 | Male 7022 | Broad elliptic | Blunt | Blunt | Slightly wavy | Intermediate | Not raised | None | Horizontal/ Semi-erect | Weak | Concave |
| 8 | Male 7028 | Elliptic | Blunt | Blunt | Slightly wavy | Intermediate | Slightly raised | None | Erect | None | Concave |
| 9 | Inbred 393-2-19 | Elliptic | Blunt | Blunt | Slightly wavy | Intermediate | Slightly raised | None | Erect | None | Concave |
| 10 | Inbred 393-2-47 | Elliptic | Blunt | Blunt | Slightly wavy | Intermediate | Slightly raised | None | Semi-erect | None | Concave |
| 11 | Marathon | Narrow elliptic | Blunt | Blunt | Very wavy | Intermediate | Slightly raised | None | Horizontal/ Semi-erect | None | Concave |
| 12 | Pinnacle | Elliptic | Blunt | Blunt | Slightly wavy | Intermediate | Slightly raised | None | Horizontal | None | Concave |

2.4A. Study #1
Head (At Market Maturity)

| # | I.D. | Head Diameter (cm) | Head Depth (cm) | Head Weight (gm) | Head Color | Head Shape |
|---|------|--------------------|------------------|-------------------|------------|------------|
| 1 | Hybrid 7007 | 17 | 13.5 | 446.3 | Blue/Green | Transverse broad elliptic |
| 2 | Hybrid 7008 | — | — | 352 | — | — |
| 3 | Hybrid 7022 | 15 | 10.5 | 377.2 | Blue/Green | Transverse narrow elliptic |
| 4 | Hybrid 7028 | 15 | 11.5 | 364.4 | Blue/Green | Transverse broad elliptic |
| 5 | Male 7007 | 10 | 8 | 93.7 | Blue/Green | Circular |
| 6 | Male 7009 | 10 | 8.5 | 126.2 | Blue/Green | Transverse broad elliptic |
| 7 | Male 7022 | 15 | 10 | 289.5 | Blue/Green | Transverse narrow elliptic |
| 8 | Male 7028 | 11 | 9.5 | 165.9 | Blue/Green | Circular |
| 9 | Inbred 393-2-19 | 13 | 10 | 325.7 | Blue/Green | Transverse elliptic |
| 10 | Inbred 393-2-47 | 11.5 | 9 | 194.7 | Blue/purple | Transverse broad elliptic |
| 11 | Marathon | 14.5 | 12.5 | 300 | Medium green | Transverse elliptic |
| 12 | Pinnacle | 14 | 9.5 | 274.6 | Medium green | Transverse elliptic |
| 13 | Male 7008 | — | — | 150 | — | — |

2.4B. Study #1
Head (At Market Maturity)

| # | I.D. | Dome Shape | Head Size | Compactness | Surface Knobbling | Bead Size | Flower Buds |
|---|------|------------|-----------|-------------|-------------------|-----------|-------------|
| 1 | Hybrid 7007 | Semi-domed | Large | Short pedicels (tight) | Fine | Medium | Even in size |
| 2 | Hybrid 7008 | — | | | | | |
| 3 | Hybrid 7022 | Very Deeply domed | Large | Short pedicels (tight) | Fine | Medium | Even in size |
| 4 | Hybrid 7028 | Semi-domed | Medium | Short pedicels (tight) | Fine | Medium | Even in size |
| 5 | Male 7007 | Domed | Small | Short pedicels (tight) | Fine | Large | Even in size |
| 6 | Male 7009 | Semi-domed | Small | Medium pedicels | Fine | Large | Even in size |

-continued

2.4B. Study #1
Head (At Market Maturity)

| # | I.D. | Dome Shape | Head Size | Compactness | Surface Knobbling | Bead Size | Flower Buds |
|---|---|---|---|---|---|---|---|
| 7 | Male 7022 | Very deeply domed | Large | Short pedicels (tight) | Fine | Medium | Even in size |
| 8 | Male 7028 | Domed | Small | Medium pedicels | Fine | Medium | Even in size |
| 9 | Inbred 393-2-19 | Deep domed | Medium | Short pedicels (tight) | Fine | Small | Even in size |
| 10 | Inbred 393-2-47 | Semi-domed | Medium | Short pedicels (tight) | Fine | Medium | Even in size |
| 11 | Marathon | Deep Domed | Medium | Short pedicels (tight) | Medium | Small | Even in size |
| 12 | Pinnacle | Deep Domed | Medium | Medium pedicels | Large | Small | Uneven in size |

2.4C. Study #1
Head (At Market Maturity) Anthocyanin Coloration

| # | I.D. | Leaf Axils | Leaf Veins | Leaf Blade | Entire Plant | Leaf Petiole |
|---|---|---|---|---|---|---|
| 1 | Hybrid 7007 | Absent | Absent | Absent | Absent | Absent |
| 2 | Hybrid 7008 | — | — | — | — | — |
| 3 | Hybrid 7022 | Absent | Absent | Absent | Absent | Absent |
| 4 | Hybrid 7028 | Absent | Absent | Absent | Absent | Absent |
| 5 | Male 7007 | Absent | Absent | Absent | Absent | Absent |
| 6 | Male 7009 | Absent | Absent | Absent | Absent | Absent |
| 7 | Male 7022 | Absent | Absent | Absent | Absent | Absent |
| 8 | Male 7028 | Absent | Absent | Absent | Absent | Absent |
| 9 | Inbred 393-2-19 | Absent | Absent | Absent | Absent | Absent |
| 10 | Inbred 393-2-47 | Slight Pressure | Absent | Absent | Absent | Absent |
| 11 | Marathon | Absent | Absent | Absent | Absent | Absent |
| 12 | Pinnacle | Absent | Absent | Absent | Absent | Absent |

2.4D. Study #1
Head (At Market Maturity)

| # | I.D. | Color of Head Leaves | Secondary Heads | Prominence of Secondary Heads | Number of Secondary Heads |
|---|---|---|---|---|---|
| 1 | Hybrid 7007 | Green | Completely Absent | Weak | 0 |
| 2 | Hybrid 7008 | — | — | — | — |
| 3 | Hybrid 7022 | Green | Completely Absent | Weak | 0 |
| 4 | Hybrid 7028 | Green | Basal | Weak | 3 |
| 5 | Male 7007 | Green | Completely Absent | Weak | 0 |
| 6 | Male 7009 | Green | Basal | Weak | 4 |
| 7 | Male 7022 | Green | Completely Absent | Weak | 0 |
| 8 | Male 7028 | Green | Completely Absent | Weak | 0 |
| 9 | Inbred 393-2-19 | Green | Completely Absent | Weak | 0 |
| 10 | Inbred 393-2-47 | Green | Completely Absent | Weak | 0 |
| 11 | Marathon | Green | Auxiliary along entire main stem up to main head | Weak | 3 |
| 12 | Pinnacle | Green | Basal | Weak | 1 |

2.5. Study #1 Flower Color

| # | I.D. | Flower Color | Flower Stalk Color |
|---|---|---|---|
| 1 | Hybrid 7007 | Yellow | Green |
| 2 | Hybrid 7008 | — | — |
| 3 | Hybrid 7022 | Yellow | Green |
| 4 | Hybrid 7028 | Yellow | — |
| 5 | Male 7007 | Yellow | — |
| 6 | Male 7009 | Yellow | — |
| 7 | Male 7022 | Yellow | Green |
| 8 | Male 7028 | Yellow | — |
| 9 | Inbred 393-2-19 | Yellow | Green |
| 10 | Inbred 393-2-47 | Yellow | Green |
| 11 | Marathon | Yellow | Green |
| 12 | Pinnacle | Yellow | Green |

4.6. Study #1 Resistance*

| # | I.D. | Downey Mildew | Buttoning | Blindness | Bolting | Brown Beads | Drought | Cold | Hollow stem | Riceyness | Whiptail |
|---|---|---|---|---|---|---|---|---|---|---|---|
| 1 | Hybrid 7007 | 9 | 8 | 8 | 5 | 9 | 7 | 5 | 8 | 9 | 9 |
| 2 | Hybrid 7008 | — | — | — | — | — | — | — | — | — | — |
| 3 | Hybrid 7022 | 9 | 8 | 8 | 4 | 8 | 7 | 3 | 8 | 9 | 9 |
| 4 | Hybrid 7028 | 9 | 8 | 8 | 4 | 9 | 7 | 4 | 8 | 9 | 9 |
| 5 | Male 7007 | 9 | 8 | 8 | 3 | 9 | 8 | 3 | 9 | 9 | 9 |
| 6 | Male 7009 | 9 | 8 | 8 | 5 | 9 | 8 | 3 | 9 | 9 | 9 |
| 7 | Male 7022 | — | 8 | 8 | 6 | 8 | 8 | 3 | 8 | 9 | 9 |
| 8 | Male 7028 | 9 | 8 | 8 | 5 | 9 | 8 | 3 | 8 | 9 | 9 |
| 9 | Inbred 393-2-19 | 9 | 8 | 8 | 6 | 9 | 8 | 6 | 9 | 9 | 9 |
| 10 | Inbred 393-2-47 | 9 | 8 | 8 | 5 | 9 | 8 | 5 | 9 | 9 | 9 |
| 11 | Marathon | 3 | 8 | 8 | 7 | 8 | 7 | 7 | 8 | 9 | 9 |
| 12 | Pinnacle | 3 | 8 | 8 | 6 | 5 | 5 | 4 | 8 | 5 | 9 |

\*1 = Most susceptible
5 = Intermediate
9 = Most resistant

2.7 Study #1 Heat Tolerance*

| # | I.D. | Heat Tolerance |
|---|---|---|
| 1 | Hybrid 7007 | 9 |
| 2 | Hybrid 7008 | — |
| 3 | Hybrid 7022 | 8 |
| 4 | Hybrid 7028 | 9 |
| 5 | Male 7007 | 9 |
| 6 | Male 7009 | 8 |
| 7 | Male 7022 | 7 |
| 8 | Male 7028 | 8 |
| 9 | Inbred 393-2-19 | 8 |
| 10 | Inbred 393-2-47 | 8 |
| 11 | Marathon | 2 |
| 12 | Pinnacle | 4 |

\*1 = Most susceptible
5 = Intermediate
9 = Most tolerant

Comparative Analysis Study #2

In a second study (Study #2) various broccoli lines were analyzed and characterized for heat tolerance. Daily high and low temperature measurements for study #2 are presented in Table 3. As in study #2, the daily temperatures were generally quite warm and on some days hot.

In study #2, the following broccoli lines were analyzed: Hybrid 7007, Hybrid 7009, Hybrid 7028, Male 7007, Male 7009, Male 7028, Inbred 393-2-19, Inbred 393-2-47, Marathon, Pinnacle, 98-2061, 98-2088, Inbred 393-2-32 and 98-2192.

In study #2, broccoli seeds were sown in the greenhouse on April 27. Broccoli seedlings were transferred to the field on June 13.

The comparative data collected in study #2 are shown in Table 4.

Table 4.1 shows the length of the harvest period, the plant and head height at harvest, the type of plant branches and the plant habit at harvest. Of particular relevance is that the broccoli plants of this invention have a significantly longer harvest period than the commercially available hybrids Marathon and Pinnacle. A longer harvest period offers growers greater flexibility in harvesting and therefore greatly reduces costs.

Tables 4.2A–4.2C show characteristics of outer leaves at harvest. Tables 4.3A–4.3B and 4.4A show characteristics of the harvested broccoli heads. Table 4.5 shows heat tolerance data.

Of particular relevance is the data in Table 4.5, which shows that the broccoli plants of this invention are heat tolerant whereas the commercially available varieties are not.

TABLE 3

Temperature Data for Study #2

| | Temperature (° F.) | | |
|---|---|---|---|
| Date | Max | min | Average |
| 08/08 | 75 | 57 | 63 |
| 08/09 | 81 | 60 | 66 |
| 08/10 | 77 | 58 | 65 |
| 08/11 | 78 | 57 | 65 |
| 08/12 | 79 | 53 | 63 |
| 08/13 | 78 | 55 | 63 |
| 08/14 | 83 | 54 | 64 |
| 08/15 | 77 | 56 | 62 |
| 08/16 | 73 | 56 | 63 |
| 08/17 | 89 | 53 | 63 |
| 08/18 | 83 | 54 | 66 |
| 08/19 | 82 | 59 | 69 |
| 08/20 | 77 | 59 | 66 |
| 08/21 | 87 | 59 | 69 |
| 08/22 | 85 | 56 | 70 |
| 08/23 | 83 | 59 | 69 |
| 08/24 | 82 | 62 | 70 |
| 08/25 | 83 | 57 | 68 |
| 08/26 | 83 | 57 | 68 |
| 08/27 | 83 | 51 | 70 |
| 08/28 | 83 | 56 | 69 |
| 08/29 | 84 | 59 | 69 |
| 08/30 | 82 | 55 | 67 |
| 08/31 | 83 | 59 | 70 |
| 09/01 | 84 | 59 | 70 |
| 09/02 | 81 | 56 | 68 |
| 09/03 | 85 | 59 | 69 |
| 09/04 | 95 | 59 | 73 |
| 09/05 | 87 | 58 | 70 |
| 09/06 | 80 | 55 | 65 |
| 09/07 | 88 | 53 | 66 |
| 09/08 | 86 | 59 | 69 |
| 09/09 | 82 | 55 | 66 |
| 09/10 | 80 | 54 | 66 |
| 09/11 | 79 | 58 | 67 |
| 09/12 | 78 | 54 | 65 |
| 09/13 | 78 | 53 | 63 |
| 09/14 | 79 | 54 | 65 |
| 09/15 | 80 | 56 | 66 |
| 09/16 | 85 | 51 | 68 |
| 09/17 | 79 | 54 | 66 |
| 09/18 | 78 | 54 | 64 |
| 09/19 | 82 | 48 | 63 |
| 09/20 | 88 | 51 | 68 |

TABLE 3-continued

Temperature Data for Study #2

| | Temperature (° F.) | | |
|---|---|---|---|
| Date | Max | min | Average |
| 09/21 | 89 | 51 | 66 |
| 09/22 | 87 | 49 | 66 |
| 09/23 | 102 | 54 | 75 |
| 09/24 | 97 | 59 | 74 |
| 09/25 | 87 | 61 | 72 |
| 09/26 | 80 | 57 | 67 |
| 09/27 | 87 | 52 | 68 |
| 09/28 | 95 | 52 | 73 |
| 09/29 | 90 | 59 | 69 |
| 09/30 | 94 | 54 | 65 |
| 10/01 | 74 | 56 | 63 |
| 10/02 | 76 | 57 | 64 |
| 10/03 | 83 | 51 | 66 |
| 10/04 | 81 | 51 | 65 |
| 10/05 | 83 | 50 | 64 |
| 10/06 | 69 | 49 | 59 |
| 10/07 | 70 | 46 | 57 |
| 10/08 | 72 | 43 | 57 |
| 10/09 | 65 | 52 | 60 |
| 10/10 | 62 | 44 | 53 |
| 10/11 | 68 | 44 | 55 |
| 10/12 | 74 | 44 | 57 |
| 10/13 | 83 | 42 | 61 |
| 10/14 | 89 | 44 | 65 |
| 10/15 | 95 | 49 | 68 |
| 10/16 | 96 | 50 | 68 |
| 10/17 | 87 | 50 | 64 |
| 10/18 | 81 | 46 | 59 |
| 10/19 | 64 | 49 | 56 |
| 10/20 | 70 | 49 | 57 |
| 10/21 | 74 | 45 | 55 |
| 10/22 | 70 | 45 | 54 |
| 10/23 | 68 | 49 | 57 |
| 10/24 | 72 | 42 | 55 |
| 10/25 | 75 | 38 | 56 |
| 10/26 | 79 | 40 | 57 |
| 10/27 | 75 | 42 | 56 |

TABLE 4

COMPARATIVE ANALYSIS Study #2
4.1. Maturity: Main Crop at 50% Harvest/Plant At Harvest

| # | I.D. | Length of Harvest Period (Days) | Plant Height (inches) | Head Height (inches) | Plant Branches | Plant Habit |
|---|---|---|---|---|---|---|
| 1 | Hybrid 7007 | 5 | 30 | 22 | Medium | Spreading |
| 2 | Hybrid 7009 | 5 | 28 ¼ | 22 | Medium | Spreading |
| 3 | Hybrid 7028 | 4 | 25 ⅝ | 17 | Medium | Spreading |
| 4 | Male 7007 | 3 | 36 | 33 | Medium | Spreading |
| 5 | Male 7009 | 4 | 37 | 25 ½ | Many | Spreading |
| 6 | Male 7028 | — | 31 | 23 ½ | Medium | Spreading |

TABLE 4-continued

COMPARATIVE ANALYSIS Study #2
4.1. Maturity: Main Crop at 50% Harvest/Plant At Harvest

| # | I.D. | Length of Harvest Period (Days) | Plant Height (inches) | Head Height (inches) | Plant Branches | Plant Habit |
|---|---|---|---|---|---|---|
| 7 | Inbred 393-2-19 | 6 | 27 | 20 | Medium | Spreading |
| 8 | Inbred 393-2-47 | 4.5 | 26 | 20 | Few | Spreading |
| 9 | Marathon | 1 | 30.5 | 20 | Many | Intermediate |
| 10 | Pinnacle | 1 | 30 | 26 ¾ | Medium | Intermediate |
| 11 | 98-2061 | 5 | 26 | 18 | Medium | Intermediate |
| 12 | 98-2088 | 4 | 29 ¼ | 23 ¾ | Medium | Intermediate |
| 13 | Inbred 393-2-32 | 6 | 27 | 18 ¼ | Medium | Intermediate |
| 14 | 98-2192 | 6 | 28 | 16 | Medium | Spreading |

4.2A. Study #2
Outer Leaves (At Harvest)

| # | I.D. | # Leaves Per Plant | Leaf Width (inches) | Leaf Length (inches) | Petiole Length (inches) | Length/width Ratio |
|---|---|---|---|---|---|---|
| 1 | Hybrid 7007 | 23 | 8 | 18 ¼ | 5 | 2:1 |
| 2 | Hybrid 7009 | 26 | 8 | 17 | 5 | 2:1 |
| 3 | Hybrid 7028 | 22 | 6 ½ | 16 | 4 ¾ | 2:1 |
| 4 | Male 7007 | 24 | 10 | 19 | 7 | 2:1 |
| 5 | Male 7009 | 32 | 9 | 21 ½ | 6 ¾ | 2:1 |
| 6 | Male 7028 | 18 | 10 ½ | 22 ½ | 6 ½ | 2:1 |
| 7 | Inbred 393-2-19 | 21 | 7 | 16 ½ | 5 ½ | 2:1 |
| 8 | Inbred 393-2-47 | 17 | 5 ¾ | 11 ¾ | 3 ½ | 2:1 |
| 9 | Marathon | 32 | 7 | 18 | 8 ¼ | 2:1 |
| 10 | Pinnacle | 25 | 5 ⅝ | 14 ½ | 7 ¼ | 2:1 |
| 11 | 98-2061 | 19 | 6 ½ | 16 ½ | 6 ¼ | 2:1 |
| 12 | 98-2088 | 28 | 7 ¼ | 14 ½ | 3 ½ | 2:1 |
| 13 | Inbred 393-2-32 | 21 | 6 ½ | 19 | 8 ¼ | 2:1 |
| 14 | 98-2192 | 28 | 8 ¼ | 18 ½ | 7 ¾ | 2:1 |

4.2B. Study #2
Outer Leaves (At Harvest)

| # | I.D. | Leaf Attachment | Wax Presence | Foliage Color | Leaf Shape | Leaf Base |
|---|---|---|---|---|---|---|
| 1 | Hybrid 7007 | Petiolate | Strong | Medium green | Elliptic | Pointed |
| 2 | Hybrid 7009 | Petiolate | Strong | Medium green | Elliptic | Blunt |
| 3 | Hybrid 7028 | Petiolate | Strong | Medium green | Elliptic | Blunt |
| 4 | Male 7007 | Petiolate | Strong | Medium green | Elliptic | Blunt |
| 5 | Male 7009 | Petiolate | Strong | Medium green | Broad elliptic | Blunt/pointed |
| 6 | Male 7028 | Petiolate | Strong | Medium green | Broad elliptic | Blunt/pointed |
| 7 | Inbred 393-2-19 | Petiolate | Strong | Medium green | Elliptic | Blunt |
| 8 | Inbred 393-2-47 | Petiolate | Strong | Medium green | Elliptic | Blunt |
| 9 | Marathon | Petiolate | Strong | Blue-green | Elliptic | Blunt |
| 10 | Pinnacle | Petiolate | Strong | Medium green | Narrow elliptic | Blunt |
| 11 | 98-2061 | Petiolate | Strong | Dark green | Elliptic | Blunt |
| 12 | 98-2088 | Petiolate | Strong | Medium green | Narrow elliptic | Blunt |

-continued

4.2B. Study #2
Outer Leaves (At Harvest)

| # | I.D. | Leaf Attachment | Wax Presence | Foliage Color | Leaf Shape | Leaf Base |
|---|---|---|---|---|---|---|
| 13 | Inbred 393-2-32 | Petiolate | Strong | Medium green | Elliptic | Blunt |
| 14 | 98-21 92 | Petiolate | Strong | Dark green | Elliptic | Blunt |

4.2C. Study #2
Outer Leaves (At Harvest)

| # | I.D. | Leaf Apex | Leaf Margins | Leaf Veins | Attitude | Torsion | Profile |
|---|---|---|---|---|---|---|---|
| 1 | Hybrid 7007 | Blunt | Slightly wavy | Intermediate | Horizontal | Weak | Planar |
| 2 | Hybrid 7009 | Blunt | Slightly wavy | Intermediate | Semi-erect/erect | Weak | Planar |
| 3 | Hybrid 7028 | Blunt | Slightly wavy | Thin | Semi-erect/erect | Weak | Planar |
| 4 | Male 7007 | Blunt | Slightly wavy | Intermediate | Semi-erect/erect | Weak | Planar |
| 5 | Male 7009 | Blunt | Very wavy | Intermediate | Semi-erect/erect | Weak | Planar/convex |
| 6 | Male 7028 | Blunt | Slightly wavy | Thick | Horizontal/semi-erect | Weak | Planar |
| 7 | Inbred 393- | Blunt | Slightly wavy | Intermediate | Semi-erect | Weak | Concave |
| 8 | Inbred 393-2-47 | Blunt erect | Slightly wavy | Intermediate | Horizontal/semi- | Weak | Concave/planar |
| 9 | Marathon | Blunt | Very wavy | Intermediate | Horizontal | Intermediate | Concave |
| 10 | Pinnacle | Blunt | Slightly wavy | Intermediate | Semi-erect/erect | Intermediate | Convex |
| 11 | 98-2061 | Blunt | Slightly wavy | Thin | Semi-erect | Weak | Planar |
| 12 | 98-2088 | Blunt | Slightly wavy | Intermediate | Semi-erect/erect | Weak | Concave |
| 13 | Inbred 393-2-32 | Blunt | Slightly wavy | Intermediate | Horizontal | Weak | Planar |
| 14 | 98-21 92 | Blunt | Slightly wavy | Intermediate | Semi-erectlerect | Weak | Planar/convex |

4.3A. Study #2
Head (At Market Maturity)

| # | I.D. | Head Diameter (inches) | Head Depth (inches) | Head Weight (gm) | Color | Head Shape |
|---|---|---|---|---|---|---|
| 1 | Hybrid 7007 | 10 | 5 ¼ | 904.9 | Blue/green | Transverse elliptic |
| 2 | Hybrid 7009 | 7 | 3 ¼ | 306.4 | Purple/blue/green | Transverse elliptic |
| 3 | Hybrid 7028 | 4 ¾ | 3 | 117 | Blue/green | Transverse elliptic |
| 4 | Male 7007 | 4 ¼ | 2 ½ | 85.6 | Medium green | Circular |
| 5 | Male 7009 | 3 ¾ | 2 ¼ | 103.6 | Dark green/ Blue/green | Transverse broad elliptic |
| 6 | Male 7028 | 6 | 3 ½ | 450.3 | Light purple/ dark green | Transverse elliptic |
| 7 | Inbred 393-2-19 | 5 | 3 | 176.3 | Blue/green purple | Transverse elliptic narrow |
| 8 | Inbred 393-2-47 | 4 ¾ | 2 ¾ | 136.4 | Light green/purple | Transverse elliptic |
| 9 | Marathon | 4 ½ | 2 ¼ | 313.1 | Yellow | Transverse elliptic |
| 10 | Pinnacle | 6 ¼ | 4 ¾ | 336.3 | Blue/green | Transverse elliptic |
| 11 | 98-2061 | 5 ½ | 3 | 184.1 | Blue/green | Transverse broad elliptic |
| 12 | 98-2088 | 5 ¾ | 3 ½ | 184.1 | Blue/green/purple | Transverse elliptic |
| 13 | Inbred 393-2-32 | 3 ¼ | 2 ½ | 67.2 | Medium green/ blue/green | Transverse broad elliptic |
| 14 | 98-2192 | 5 ½ | 3 | 226.0 | Blue/green | Transverse elliptic |

4.3B. Study #2
Head (At Market Maturity)

| # | I.D. | Dome Shape | Head Size | Compactness | Surface Knobbling | Beads Size | Flower Buds |
|---|---|---|---|---|---|---|---|
| 1 | Hybrid 7007 | Domed | Large | Medium pedicels | Medium | Medium/large | Even in size |
| 2 | Hybrid 7009 | Deep-domed | Medium | Medium pedicels | Medium | Medium | Even in size |
| 3 | Hybrid 7028 | Semi-domed | Medium | Short pedicels | Medium | Small | Even in size |
| 4 | Male 7007 | Domed | Small | Medium pedicels | Fine | Medium | Even in size |
| 5 | Male 7009 | Deep-domed | Small | Short pedicels | Fine | Small | Even in size |
| 6 | Male 7028 | Deep-domed | Medium | Short pedicels | Medium | Small | Even in size |
| 7 | Inbred 393-2-19 | Deep-domed | Medium | Short pedicels | Medium | Small | Even in size |
| 8 | Inbred 393-2-47 | Domed | Medium | Short pedicels | Medium | Small | Even in size |
| 9 | Marathon | Domed | Small | Short pedicels | Medium | Small | Uneven in size |
| 10 | Pinnacle | Domed | Medium | Long pedicels | Coarse | Large | Uneven in size |
| 11 | 98-2061 | Semi-domed | Medium | Short pedicels | Medium | Small | Even in size |
| 12 | 98-2088 | Semi-domed | Medium | Medium pedicels | Medium | Medium | Even in size |
| 13 | Inbred 393-2-32 | Semi-domed | Small | Short pedicels | Fine | Small | Even in size |
| 14 | 98-2192 | Deep-domed | Medium | Short pedicels | Medium | Small | Even in size |

4.4A. Study #2
Head (At Market Maturity)

| # | I.D. | Color of Head Leaves | Secondary Heads | Prominence of Secondary Heads | # of Secondary Heads |
|---|---|---|---|---|---|
| 1 | Hybrid 7007 | — | — | — | — |
| 2 | Hybrid 7009 | — | — | — | — |
| 3 | Hybrid 7028 | — | Basal | Weak | 1 |
| 4 | Male 7007 | — | Basal | Weak | 0 |
| 5 | Male 7009 | Green | — | — | — |
| 6 | Male 7028 | — | — | — | — |
| 7 | Inbred 393-2-19 | — | — | — | — |
| 8 | Inbred 393-2-47 | — | — | — | — |
| 9 | Marathon | — | Completely absent | Weak | 0 |
| 10 | Pinnacle | — | Basal | Weak | 3 |
| 11 | 98-2061 | — | Basal | Weak | 1 |
| 12 | 98-2088 | — | Basal | Intermediate | 4 |
| 13 | Inbred 393-2-32 | — | — | — | — |
| 14 | 98-2192 | — | Combination | Intermediate | 3 |

4.5. Study #2
Heat Tolerance

| # | I.D. | Heat Tolerance* |
|---|---|---|
| 1 | Hybrid 7007 | 7 |
| 2 | Hybrid 7009 | 8 |
| 3 | Hybrid 7028 | 7 |
| 4 | Male 7007 | — |
| 5 | Male 7009 | 7/8 |
| 6 | Male 7028 | — |
| 7 | Inbred 393-2-19 | 5/6 |
| 8 | Inbred 393-2-47 | 5/6 |
| 9 | Marathon | 2 |
| 10 | Pinnacle | 1 |
| 11 | 98-2061 | 7/8 |
| 12 | 98-2088 | 7 |
| 13 | Inbred 393-2-32 | — |
| 14 | 98-2192 | 8/9 |

*1 = Most susceptible
5 = Intermediate
9 = Most tolerant

Comparative Analysis Study #3

In a third study (Study #3) various broccoli lines were analyzed and characterized for heat tolerance. Daily high and low temperature measurements for study #3 are presented in Table 5. As in studies #'s 1 and 2, the growth temperatures during study #3 were generally quite warm and sometimes hot.

Various broccoli lines were analyzed for heat tolerance. The data is presented in Table 6.

The commercial hybrids (Marathon, Pinnacle, Premium Crop, Patriot, Laguna, MonteCristo, Greenbelt, Everest, CMS Liberty, and Landmark) averaged a score of 2.83 for heat tolerance. The new heat tolerant hybrids (7007, 7009, and 7028) that are the subject of this patent application averaged 7.00 for heat tolerance. The heat tolerance scale goes from one (1) to ten (10), with one (1) the most susceptible and ten (10) very highly resistant. In general, ratings of five (5) or below are unmarketable in a heat stress growth condition and represent significant economic loss to the broccoli growers if such a level of heat stress reaction occurs in their broccoli fields.

TABLE 5

Temperature Data for Study #3

| Date | Temperature (° F.) | | |
|---|---|---|---|
| | Max | min | Average |
| 07/03 | 79 | 47 | 62 |
| 07/04 | 84 | 48 | 63 |
| 07/05 | 75 | 52 | 60 |
| 07/06 | 75 | 52 | 62 |
| 07/07 | 75 | 52 | 61 |
| 07/08 | 71 | 48 | 59 |
| 07/09 | 63 | 54 | 58 |
| 07/10 | 70 | 54 | 59 |
| 07/11 | 73 | 53 | 59 |
| 07/12 | 74 | 52 | 59 |
| 07/13 | 85 | 53 | 65 |
| 07/14 | 87 | 54 | 69 |
| 07/15 | 82 | 50 | 63 |
| 07/16 | 72 | 32 | 62 |
| 07/17 | 76 | 56 | 64 |
| 07/18 | 83 | 58 | 68 |
| 07/19 | 89 | 52 | 69 |
| 07/20 | 83 | 53 | 67 |
| 07/21 | 88 | 53 | 71 |
| 07/22 | 100 | 55 | 78 |
| 07/23 | 99 | 59 | 77 |
| 07/24 | 88 | 56 | 69 |
| 07/25 | 95 | 54 | 72 |
| 07/26 | 81 | 58 | 70 |
| 07/27 | 76 | 55 | 63 |
| 07/28 | 78 | 55 | 62 |
| 07/29 | 75 | 56 | 62 |
| 07/30 | 72 | 56 | 61 |
| 07/31 | 72 | 57 | 62 |
| 08/01 | 82 | 57 | 65 |
| 08/02 | 83 | 56 | 65 |
| 08/03 | 88 | 54 | 68 |
| 08/04 | 83 | 56 | 66 |
| 08/05 | 77 | 56 | 64 |
| 08/06 | 74 | 58 | 64 |
| 08/07 | 79 | 59 | 66 |
| 08/08 | 90 | 56 | 71 |
| 08/09 | 98 | 59 | 74 |
| 08/10 | 109 | 60 | 81 |
| 08/11 | 100 | 61 | 78 |
| 08/12 | 91 | 58 | 70 |
| 08/13 | 83 | 56 | 66 |
| 08/14 | 84 | 52 | 64 |
| 08/15 | 81 | 50 | 62 |
| 08/16 | 86 | 50 | 66 |
| 08/17 | 92 | 53 | 71 |
| 08/18 | 98 | 58 | 75 |
| 08/19 | 97 | 60 | 75 |

TABLE 5-continued

Temperature Data for Study #3

| Date | Temperature (° F.) | | |
|---|---|---|---|
| | Max | min | Average |
| 08/20 | 92 | 57 | 71 |
| 08/21 | 89 | 58 | 68 |
| 08/22 | 74 | 54 | 61 |
| 08/23 | 74 | 53 | 61 |
| 08/24 | 72 | 51 | 61 |
| 08/25 | 69 | 53 | 60 |
| 08/26 | 71 | 52 | 60 |
| 08/27 | 77 | 54 | 63 |
| 08/28 | 81 | 50 | 63 |
| 08/29 | 86 | 51 | 67 |
| 08/30 | 87 | 50 | 67 |
| 08/31 | 83 | 51 | 64 |
| 09/01 | 69 | 54 | 59 |
| 09/02 | 81 | 51 | 61 |
| 09/03 | 91 | 48 | 64 |
| 09/04 | 95 | 52 | 71 |
| 09/05 | 94 | 46 | 72 |
| 09/06 | 95 | 57 | 71 |
| 09/07 | 91 | 55 | 69 |
| 09/08 | 93 | 54 | 71 |
| 09/09 | 98 | 54 | 69 |
| 09/10 | 91 | 58 | 71 |
| 09/11 | 83 | 61 | 69 |
| 09/12 | 89 | 64 | 73 |
| 09/13 | 95 | 68 | 77 |
| 09/14 | 93 | 64 | 75 |
| 09/15 | 77 | 56 | 64 |
| 09/16 | 68 | 56 | 60 |
| 09/17 | 83 | 32 | 70 |
| 09/18 | 85 | 52 | 67 |
| 09/19 | 87 | 55 | 69 |
| 09/20 | 88 | 57 | 68 |
| 09/21 | 76 | 55 | 62 |
| 09/22 | 73 | 53 | 61 |
| 09/23 | 72 | 52 | 60 |
| 09/24 | 71 | 51 | 59 |
| 09/25 | 65 | 54 | 59 |
| 09/26 | 65 | 49 | 57 |
| 09/27 | 71 | 46 | 46 |
| 09/28 | 73 | 52 | 60 |
| 09/29 | 64 | 48 | 57 |
| 09/30 | 70 | 56 | 59 |
| 10/01 | 63 | 56 | 58 |
| 10/02 | 69 | 47 | 59 |
| 10/03 | 69 | 44 | 55 |
| 10/04 | 76 | 43 | 58 |
| 10/05 | 83 | 44 | 63 |
| 10/06 | 87 | 47 | 65 |
| 10/07 | 78 | 45 | 60 |
| 10/08 | 74 | 51 | 61 |
| 10/09 | 72 | 43 | 57 |
| 10/10 | 75 | 45 | 57 |
| 10/11 | 78 | 40 | 56 |
| 10/12 | 73 | 46 | 58 |
| 10/13 | 75 | 45 | 59 |
| 10/14 | 69 | 32 | 59 |
| 10/15 | 71 | 40 | 54 |
| 10/16 | 74 | 43 | 57 |
| 10/17 | 77 | 39 | 57 |

TABLE 6

Comparative Analysis: Study #3

| # | Field Row No | ID | Heat Tolerance (0–9)** |
|---|---|---|---|
| 1 | 2001 | Marathon | 1 |
| 2 | 2002 | Pinnacle | 3 |
| 4 | 2004 | H7009 | 8 |

TABLE 6-continued

Comparative Analysis: Study #3

| # | Field Row No | ID | Heat Tolerance (0–9)** |
|---|---|---|---|
| 5 | 2005 | Prem Crop | 4− |
| 6 | 2006 | H7007 | 7+ |
| 8 | 2008 | H7028 | 6 |
| 9 | 2009 | Patriot | 1 |
| 10 | 2010 | H7010 | |
| 11 | 2011 | Laguna | 5 |
| 12 | 2012 | H7021R | 5− |
| 13 | 2013 | Montecristo | 4.1 |
| 14 | 2014 | Greenbelt | 3− |
| 15 | 2015 | H7007 | |
| 16 | 2016 | H7009 | |
| 17 | 2017 | H7028 | |
| 18 | 2019 | 96-7829/7770 | 5− |
| 19 | 2020 | H7021R | |
| 20 | 2021 | 96-7829/7778 | 6− |
| 21 | 2022 | Greenbelt | |
| 22 | 2023 | 96-7829/7861 | 6 |
| 23 | 2024 | Sultan | 2.5 |
| 26 | 2029 | Tierra | 6− |
| 27 | 2030 | Laguna | |
| 28 | 2031 | 96-7829/7864 | |
| 29 | 2032 | 96-7829/7865 | 4+ |
| 30 | 2033 | Fiesta | |
| 31 | 2034 | Everest | 2 |
| 32 | 2035 | Liberty | 2+ |
| 33 | 2036 | Marathon | 3 |
| 34 | 2037 | 96-7881/7790 | 7− |
| 35 | 2038 | 96-7881/7887 | |
| 36 | 2039 | 96-7770-2/7825 | 6 |
| 37 | 2040 | 96-7770/7935 | 6 |
| 38 | 2041 | 96-7770/7935 | 6 |
| 39 | 2042 | 96-7770/7887 | 7− |
| 40 | 2043 | Landmark | 2 |
| 41 | 2044 | H7009 | 7 |
| 42 | 2045 | 96-8092/7825 | 3 |
| 43 | 2046 | 96-8092/7795 | 4+ |
| 44 | 2047 | 96-8092/7883 | |
| 45 | 2049 | 96-8030/7935 | |
| 46 | 2050 | 96-8030/7914 | |
| 47 | 2051 | H7007 | 7− |
| 48 | 2053 | Pinnacle | 2+ |
| 49 | 2054 | Greenbelt | 2 |
| 50 | 2055 | 97-1705/1692 | 7− |
| 51 | 2056 | 97-1705/1524 | |

**0 = Most susceptible
5 = Intermediate
9 = Most tolerant

Transgenic Broccoli

The broccoli varieties of this invention can be transformed with useful genes to make heat tolerant transgenic broccoli varieties. Such useful genes include herbicide resistant genes, virus resistant genes and the like.

To introduce isolated genes or a group of genes into the genome of plant cells such as broccoli an efficient host gene vector system is necessary. The foreign genes should be expressed in the transformed plant cells and stably transmitted (somatically and sexually) to the next generation of cells produced. The vector should be capable of introducing, maintaining and expressing a gene in plant cells, from a variety of sources, including but not limited to plants and animals, bacteria, fungi, yeast or virus. Additionally it should be possible to introduce the vector into a wide variety of plants. The location of the new gene in the plant genome may be important in determining effective gene expression of the genetically engineered plant. In addition, to be effective, the new gene must be passed on to progeny by normal breeding.

Directed genetic modification and expression of foreign genes in dicotyledonous (broad-leafed) plants such as tobacco, broccoli, potato and alfalfa has been shown to be possible using the T-DNA of the tumor-inducing (Ti) plasmid of Agrobacterium turnefaciens. Using recombinant DNA techniques and bacterial genetics, foreign pieces of DNA can be inserted into T-DNA in Agrobacterium. Following infection by the bacterium or Ti plasmid, the foreign DNA is inserted into the host plant chromosomes, thus producing a genetically engineered cell and eventually a genetically engineered plant. A second approach is to introduce root-inducing (Ri) plasmids as the gene vectors.

Biological material can be isolated from the seeds and plants of this invention by procedures well known in the art. Such material may include but is not limited to DNA, RNA, protein and carbohydrates. The DNA may include one or more genes. The genes may encode proteins involved in heat tolerance.

Deposit Information

Representative of, but not limiting the invention, Applicants have deposited seeds from M7028, M7007, M7009 and 393-2-19 with the American Type Culture Collection.

Applicants have made available to the public without restriction a deposit of at least 2500 seeds of broccoli M7028 on Dec. 17, 1998 with the American Type Culture Collection (ATCC), Rockville, Md. 20852 which has been assigned ATCC number 203530.

Applicants have made available to the public without restriction a deposit of at least 2500 seeds of broccoli M7007 on Dec. 17, 1998 with the American Type Culture Collection (ATCC), Rockville, Md. 20852 which has been assigned ATCC number 203531.

Applicants have made available to the public without restriction a deposit of at least 2500 seeds of broccoli M7009 on Dec. 17, 1998 with the American Type Culture Collection (ATCC), Rockville, Md. 20852 which has been assigned ATCC number 203532.

Applicants have made available to the public without restriction a deposit of at least 2500 seeds of broccoli 393-2-19 on Dec. 17, 1998 with the American Type Culture Collection (ATCC), Rockville, Md. 20852 which has been assigned ATCC number 203533.

The deposits will be maintained in the ATCC depository, which is a public depository, for a period of 30 years, or 5 years after the most recent request, or for the effective life of the patent, whichever is longer, and will be replaced if a deposit becomes nonviable during that period.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

We claim:

1. A broccoli seed designated 393-2-19 and having ATCC Accession Number 203533.

2. A broccoli plant or its parts produced by the seed of claim 1.

3. A regenerated broccoli plant regenerated from tissue culture of the broccoli plant of claim 2 wherein said regenerated plant comprises a center head having a diameter of 3 to 8 inches at maturity when said regenerated plant is exposed to a maximum temperature of at least 85° F. for 15 days during the growth cycle of said regenerated plant.

4. Progeny seed produced from crossing the plant of claim 2 with another broccoli plant wherein said progeny seed produces a progeny plant comprising a center head having a diameter of 3 to 8 inches at maturity when said progeny plant is exposed to a maximum temperature of at least 85° F. for 15 days during the growth cycle of said progeny plant.

5. Tissue culture according to claim 3 comprising regenerable cells selected from the group consisting of meristematic tissue, anthers, leaves, ovules, roots, embryos, protoplasts and pollen.

6. A regenerated broccoli plant regenerated from regenerable cells of a tissue culture according to claim 5 wherein said regenerated plant comprises a center head having a diameter of 3 to 8 inches at maturity when said plant is exposed for a maximum temperature of at least 85° F. for 15 days during the growth cycle of said plant.

7. A broccoli plant having all the phenotypic characteristics of a plant produced from the seed of claim 1.

8. A seed from said plant of claim 7.

9. A broccoli plant produced from the progeny seed of claim 4.

10. F1 progeny seed produced from crossing the plant of claim 2 with another broccoli plant.

11. F1 progeny seed produced from crossing the plant of claim 7 with another broccoli plant.

12. Progeny seeds produced from crossing the plant of claim 2 with another broccoli plant wherein said progeny seeds produce progeny plants comprising center heads having a diameter of 3 to 8 inches at maturity when said progeny plants are exposed to a maximum temperature of at least 85° F. for 15 days during the growth cycle of said progeny plants.

* * * * *